(12) United States Patent
Gabriele et al.

(10) Patent No.: US 10,822,450 B2
(45) Date of Patent: *Nov. 3, 2020

(54) POLY(GLYCEROL SEBACATE)-INTERLEUKIN INHIBITOR COPOLYMERS AND METHODS OF MAKING AND USE

(71) Applicant: THE SECANT GROUP, LLC, Telford, PA (US)

(72) Inventors: Peter D. Gabriele, Frisco, TX (US); Carissa Smoot, Harleysville, PA (US); Charles Brendan Nicholson, Coopersburg, PA (US); Jeremy J. Harris, Buckingham, PA (US)

(73) Assignee: THE SECANT GROUP LLC, Telford, PA (US)

( * ) Notice: Subject to any disclaimer, the term of this patent is extended or adjusted under 35 U.S.C. 154(b) by 58 days.

This patent is subject to a terminal disclaimer.

(21) Appl. No.: 16/032,733

(22) Filed: Jul. 11, 2018

(65) Prior Publication Data

US 2019/0016854 A1     Jan. 17, 2019

Related U.S. Application Data

(60) Provisional application No. 62/531,132, filed on Jul. 11, 2017.

(51) Int. Cl.
| | | |
|---|---|---|
| *C08G 63/12* | (2006.01) | |
| *A61K 47/55* | (2017.01) | |
| *C08G 63/81* | (2006.01) | |
| *C08G 63/133* | (2006.01) | |
| *C08G 63/123* | (2006.01) | |
| *C08G 63/06* | (2006.01) | |
| *C08G 63/78* | (2006.01) | |
| *A61K 47/59* | (2017.01) | |

(52) U.S. Cl.
CPC .............. *C08G 63/12* (2013.01); *A61K 47/55* (2017.08); *C08G 63/065* (2013.01); *C08G 63/123* (2013.01); *C08G 63/133* (2013.01); *C08G 63/785* (2013.01); *C08G 63/81* (2013.01); *A61K 47/593* (2017.08); *C08G 2230/00* (2013.01)

(58) Field of Classification Search
CPC ............................ A61K 47/55; A61K 47/593
See application file for complete search history.

(56) References Cited

U.S. PATENT DOCUMENTS

| | | | |
|---|---|---|---|
| 4,632,964 A | 12/1986 | Altschuler et al. | |
| 4,664,978 A | 5/1987 | Wu et al. | |
| 6,017,566 A | 1/2000 | Bunczek et al. | |
| 6,444,782 B1 | 9/2002 | Hamlin | |
| 7,645,504 B1 | 1/2010 | Pacetti | |
| 7,722,894 B2 | 5/2010 | Wang et al. | |
| 8,716,410 B2 | 5/2014 | Venkatraman et al. | |
| 9,359,472 B2 | 6/2016 | Nicholson et al. | |
| 2006/0009839 A1 | 1/2006 | Tan | |
| 2009/0214373 A1 | 8/2009 | Stinson et al. | |
| 2011/0038910 A1 | 2/2011 | Faucher et al. | |
| 2013/0295012 A1* | 11/2013 | Ingber ................. A61K 9/1617 | |
| | | | 424/9.1 |
| 2015/0344618 A1* | 12/2015 | Nicholson ............. C08G 63/81 | |
| | | | 424/94.63 |
| 2016/0242895 A1 | 8/2016 | Matheny | |

FOREIGN PATENT DOCUMENTS

| | | |
|---|---|---|
| EP | 0618249 A3 | 3/1994 |
| WO | 2009009749 A1 | 1/2009 |
| WO | 2009067482 A1 | 5/2009 |
| WO | 00/55236 A1 | 9/2009 |
| WO | 2013154780 A1 | 10/2013 |
| WO | 2015184313 A1 | 3/2015 |

OTHER PUBLICATIONS

T.Wersig et al "Poly(glycerol adipate)—indomethacin drug conjugates—synthesis and in vitro characterization", International Journal of Pharmaceutics 531 (2017) 225-234, Aug. 2017 (Year: 2017).*
Suksiriworaponga et al "Synthesis and properties of a biodegradable polymer-drug conjugate: Methotrexate-poly(glycerol adipate)" Colloids and Surfaces B: Biointerfaces 167 (2018) 115-125 (Year: 2018).*
Benoit Louage et al: "Poly(glycerol sebacate) nanoparticles for encapsulation of hydrophobic anti-cancer drugs", Polymer Chemistry, vol. 8, No. 34, Jan. 1, 2017 (Jan. 1, 2017), pp. 5033-5038, XP055490867, GB ISSN: 1759-9954,DOI: 10.1039/C6PY02192A.
Guo et. al., "Characterization and optimization of glycerol/sebacate ratio in poly(glycerol-sebacate elastomer for cell culture application", J. Biomed. Mater. Res. Part A, vol. 102A, pp. 3903-3907, 2014.

(Continued)

*Primary Examiner* — Ling Siu Choi
*Assistant Examiner* — Gennadiy Mesh
(74) *Attorney, Agent, or Firm* — McNees Wallace & Nurick LLC (57) ABSTRACT

A method of preparing a polymeric material includes combining a glycerol-pharmaceutical conjugate, glycerol, and water in a vessel. The glycerol-pharmaceutical conjugate includes a pharmaceutical compound, for example, salicylic acid, having at least one carboxyl group attached to glycerol by an ester bond. The method also includes adding sebacic acid to the vessel and removing water from the vessel and reacting the glycerol, glycerol-pharmaceutical conjugate, and sebacic acid in the vessel at atmospheric pressure in the presence of an inert gas. The method further includes applying a sub-atmospheric pressure to the vessel after the step of reacting, to form the polymeric material in the vessel. The polymeric material includes a polyester copolymer of the sebacic acid and the glycerol and the pharmaceutical compound.

7 Claims, 8 Drawing Sheets

(56) References Cited

OTHER PUBLICATIONS

Gao et. al., "Macroporous Elastomeric Scaffolds with Extensive Micropores for Soft Tissue Engineering", Wallace H. Coulter Department of Biomedical Engineering, Georgia Institute of Technology, vol. 12, pp. 917-925, 2010.

Jaafar et. al., "Spectroscopic evaluation, thermal, and thermomechanical characterization of poly(glycerol-sebacate) with variations in curing temperatures and durations", J. Mater. Sci., vol. 45, pp. 2525-2529, 2009.

Pryor et. al., "Poly(glycerol sebacate) films prevent postoperative adhesions and allow laparoscopic placement", Surgery, vol. 146, pp. 490-497, 2009.

Sun et. al., "The influence of lactic acid on the properties of Poly (glycerol-sebacate-lactic acid)", Materials Science and Engineering C, vol. 29, pp. 178-182, 2009.

Chen et. al., "Characterisation of a soft elastomer poly(glycerol sebacate) designed to match the mechanical properties of myocardial tissue", Biomaterials, vol. 29, pp. 47-57, 2008.

Barrere et al., "Polyester synthesis in aqueous miniemulsions", Polymer, vol. 44, pp. 2833-2841, 2003.

Wang, et. al., "A Tough Biodegradable Elastomer", Nature Biotechnology, vol. 20, pp. 602-606, 2002.

Erdmann, "Synthesis and degradation characteristics of salicylic acid-derived poly(anhydride-esters)", Biomaterials, vol. 21, pp. 1941-1946, 2000.

Group, "What is Caravacrol? 8 Facts to Know", downloaded May 21, 2018 from https://www.globalhealingcenter.com/natural-health/what-is-carvacrol-8-facts-to-know/, 3 pages.

Jayatilaka et al., "Synergistic IL-6 and IL-8 paracrine signaling pathway infers a strategy to inhibit tumour cell migration", Nature Communications, 12 pages, 2017.

Liu et al., "Structure and Properties of Thermoplastic Poly(glycerol sebacate) Elastomers Originating from Prepolymers with Different Molecular Weights", Journal of Applied Polymer Science, vol. 104, pp. 1131-1137, 2007.

Nguyen, "Smuggling essential oils into enemy biofilms", Chemical & Engineering News, p. 10, May 21, 2018.

Sun et al., "Glycolic acid modulates the mechanical property and degradation of poly(glycerol sebacate glycolic acid)", J. Biomed. Mater. Res. A, vol. 92, pp. 332-339, 2010.

Tian et al., "Aspirin promotes apoptosis in a murine model of colorectal cancer by mechanisms involving downregulation of IL-6-STAT3 signaling pathway", Int. J. Colorectal Dis., vol. 26, pp. 13-22 (2011).

Yang et al., "Aspirin inhibits monocyte chemoattractant protein-1 and interleukin-8 expression in TNF-α stimulated human umbilical vein endothelial cells", Atherosclerosis, vol. 174, pp. 207-213, 2004.

\* cited by examiner

POLY(GLYCEROL SEBACATE)-INTERLEUKIN INHIBITOR COPOLYMERS AND METHODS OF MAKING AND USE

CROSS-REFERENCE TO RELATED APPLICATIONS

This application claims priority to and the benefit of U.S. Provisional Application No. 62/531,132 filed Jul. 11, 2017, which is hereby incorporated by reference in its entirety.

FIELD OF THE INVENTION

The present disclosure is generally directed to copolymers of polyesters and pharmaceutical compounds and methods of making and using copolymers of polyesters and pharmaceutical compounds. More specifically, the present disclosure is directed to copolymers of poly(glycerol sebacate) and interleukin inhibitors and methods of making and using copolymers of poly(glycerol sebacate) and interleukin inhibitors.

BACKGROUND OF THE INVENTION

Poly(glycerol sebacate) (PGS) is a cross-linkable elastomer formed as a co-polymer from glycerol and sebacic acid. PGS is biocompatible and biodegradable, reduces inflammation, improves healing, and has antimicrobial properties, all of which make it useful as a biomaterial in the biomedical field.

Acetylsalicylic acid (aspirin) has analgesic, antithrombotic, and anti-inflammatory properties. More recently, long-term daily aspirin regimens have been associated with a lower incidence in several cancers. The active mechanism involving aspirin's anti-inflammatory and analgesic action is inhibition of Interleukin-6 (IL-6) and Interleukin-8 (IL-8) (interleukin+) chemokine release.

Jayatilaka et al. ("Synergistic IL-6 and IL-8 paracrine signaling pathway infers a strategy to inhibit tumour cell migration", Nature Communications, DOI: 10.1038/ncomms15584, May 26, 2017) recently reported that cancer metastasis from solid tumors is initiated by the solid tumor production of IL-6 and IL-8 and that metastatic inhibition of IL-6 and Il-8 by chemotherapeutic drugs designed to specifically inhibit IL-6 and IL-8 action held off the metastatic behavior. Aspirin, however, is not discussed or mentioned by Jayatilaka.

Aspirin is presently not available in therapeutic form. Aspirin is metabolized by the body to salicylic acid, which also has analgesic and anti-inflammatory properties. Neither aspirin nor salicylic acid can be introduced directly into the blood stream.

Carvacrol is a monoterpenoid phenol present in the essential oil of certain plants, including oregano. Carvacrol may have anti-inflammatory properties and act as an interleukin inhibitor.

BRIEF DESCRIPTION OF THE INVENTION

What is needed is a biodegradable, biocompatible polymer that provides a controlled release of a pharmaceutical compound, more specifically an interleukin inhibitor.

In an embodiment, a method of preparing a polymeric material includes combining an alcohol-pharmaceutical conjugate, a polyol, and an aqueous liquid in a vessel. The alcohol-pharmaceutical conjugate includes a pharmaceutical compound having at least one carboxyl group attached to the polyol by an ester bond. The method also includes adding an acid monomer to the vessel and heating and removing water from the vessel to produce the polymeric material. The polymeric material includes a polyester copolymer of the acid monomer and the polyol and the pharmaceutical compound.

In another embodiment, a method of preparing a polymeric material includes combining glycerol, a glycerol-pharmaceutical conjugate, and water in a vessel. The glycerol-pharmaceutical conjugate includes a pharmaceutical compound having at least one carboxyl group attached to the glycerol by an ester bond. The method also includes then adding sebacic acid to the vessel and then removing water from the vessel. The method further includes then reacting the glycerol, glycerol-pharmaceutical conjugate, and sebacic acid in the vessel at atmospheric pressure and a temperature in the range of 50–200° C. in the presence of an inert gas for a period of about 1 hour to about 48 hours. The method includes then applying a sub-atmospheric pressure to the vessel for about 1 hour to about 76 hours after the step of reacting in the presence of an inert gas at atmospheric pressure, with a temperature in the vessel in the range of 50-200° C., thereby forming the polymeric material in the vessel. The polymeric material includes a polyester copolymer of the acid monomer and the polyol and the pharmaceutical compound.

In yet another embodiment, a polymeric material includes a polyester copolymer of an acid monomer and a polyol and a pharmaceutical compound. The polymeric material is formed by a method including combining an alcohol-pharmaceutical conjugate, a polyol, and an aqueous liquid in a vessel. The alcohol-pharmaceutical conjugate includes a pharmaceutical compound having at least one carboxyl group attached to the polyol by an ester bond. The method also includes adding an acid monomer to the vessel and heating and removing water from the vessel to produce the polymeric material.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are compositions and methods of formation and use of a polymeric material including a polyester of an acid monomer and a polyol and a pharmaceutical compound.

Exemplary embodiments provide polymeric compositions that may serve as or be formed into biodegradable, biocompatible, implantable structures that degrade to provide controlled release of a pharmaceutical compound from the polymeric composition.

Embodiments of the present disclosure, for example, in comparison to concepts failing to include one or more of the features disclosed herein, provide biodegradable, biocompatible polymeric materials with high loading of a pharmaceutical compound; provide biodegradable, biocompatible, implantable structures of polymeric compositions from thermoset polymeric compositions; provide controlled release of a pharmaceutical compound from biodegradable, biocompatible, implantable structures; provide linear release of pharmaceutical compounds by surface erosion of biodegradable, biocompatible, implantable structures; provide a therapeutic controlled release delivery device for the active of an IL-6 or IL-8 inhibitor anti-metastatic therapy in a polymer construct or polymer microparticle; expand or extend salicylic acid products; permit incorporation of chemotherapeutic active pharmaceutical ingredients into polymer microspheres; provide the therapeutic value of PGS-salicylic acid in coatings and/or adhesives for medical devices or in prophylactic applications; or combinations thereof.

The loading limit of a polymer by conjugation of a pharmaceutical compound is generally fairly low, typically less than 1% by total weight of the conjugated polymer, as there are a limited number of reactive site, steric issues with the pharmaceutical compound reaching those reactive sites of the polymer, and solvent compatibility issues between the polymer and the pharmaceutical compound.

In exemplary embodiments, high loading of polyester copolymer systems with pharmaceutical compounds are achieved by first reacting the pharmaceutical compound with a first monomer of the polyester copolymer to form a monomer-pharmaceutical conjugate with a high yield. This monomer-pharmaceutical conjugate is then combined with additional first monomer and with second monomer to form a polyester copolymer system with high loading of the pharmaceutical compound. The first and second monomers are a polyol and an acid monomer. Pharmaceutical loadings of at least 25% by total weight of the copolymer may be achieved. The pharmaceutical compound may be present at a loading, by weight, with respect to the total weight of the copolymer, of up to about 25%, at least 1% at least 2%, at least 5%, at least 10%, at least 15%, at least 20%, at least 25%, about 1% to about 25%, about 2% to about 25%, about 5% to about 25%, about 10% to about 25%, about 15% to about 25%, about 20% to about 25%, about 1% to about 5%, about 2% to about 5%, about 5% to about 10%, about 10% to about 15%, about 15% to about 20%, or any value, range, or sub-range therebetween.

Surprisingly, in some embodiments, these polyester-pharmaceutical copolymer systems have many similar physical and/or chemical characteristics to the polyester copolymer system without the pharmaceutical compounds, even at high loadings, including, but not limited to, a similar weight average molecular weight, a similar low polydispersity index, or a similar linear hydrolysis rate. Qualitatively, however, PGS-salicylic acid was observed to be stiffer and less tacky than PGS. Surprisingly, in some embodiments, these polyester copolymer systems had a lower polydispersity than the polydispersity of the polyester copolymer itself without a pharmaceutical compound in certain instances. Thermosets of these systems provided a sustained controlled release of the pharmaceutical compound by degradation of the thermoset after an initial bolus release.

Polyester copolymer systems with pharmaceutical compounds formed by combining the pharmaceutical compound with the formed polyester copolymer produced much lower loading yields at much lower loading levels. In contrast to the highly-loaded polyester copolymer systems, thermosets of these systems were also found to break apart at a relatively early stage of degradation rather than providing a sustained controlled release of the pharmaceutical compound.

In some embodiments, a polyester-pharmaceutical copolymer is formed in a process that includes forming a monomer-pharmaceutical conjugate by combining a first monomer and an aqueous liquid in a vessel, adding a pharmaceutical compound to the vessel, and heating and removing water from the vessel to produce the monomer-pharmaceutical conjugate. The pharmaceutical compound includes at least one hydroxyl group or at least one carboxyl group. The monomer-pharmaceutical conjugate includes the pharmaceutical compound attached to the first monomer by an ester bond.

The process further includes combining the monomer-pharmaceutical conjugate, additional first monomer, and an aqueous liquid in a vessel, adding a second monomer to the vessel, and heating and removing water from the vessel to produce the polymeric material. The polymeric material comprises a polyester copolymer of the first monomer and the second monomer and the pharmaceutical compound.

As used herein the term "vessel" may refer to a beaker, bottle, canister, flask, bag, receptacle, tank, vat, jar, vial, tube, or the like that are generally known in the art to contain fluids or fluid-like materials and liquids.

In some embodiments, the first monomer is a polyol, and the second monomer is an acid monomer. In other embodiments, the first monomer is an acid monomer, and the second monomer is a polyol.

In some embodiments, the polyol is a polyol monomer. In some embodiments, the polyol is a diol monomer. In some embodiments, the polyol is a triol monomer. In some embodiments, the polyol is glycerol.

In some embodiments, the acid monomer is a diacid monomer. The diacid monomer may include a compound of the formula [HOOC(CH$_2$)$_n$COOH], where n=1-30. In some embodiments, the acid monomer may include malonic acid, succinic acid, glutaric acid, adipic acid, pimelic acid, suberic acid, azelaic acid, sebacic acid, or a combination thereof. In some embodiments, the diacid is sebacic acid.

In some embodiments, the aqueous liquid is water.

The pharmaceutical compound may be any pharmaceutical compound that includes at least one hydroxyl group, carboxyl group, or primary amine group and that does not sterically prevent copolymerization of the first monomer and the second monomer. Pharmaceutical compounds may include, but are not limited to, an interleukin inhibitor, a vitamin, an anti-inflammatory agent, a protein, a protease, an herbicide, an aquarium food source, an anti-mitotic agent, an anti-platelet agent, an anti-coagulant agent, an anti-thrombotic agent, a thrombolytic agent, an enzyme, a chemotherapeutic agent, an antibiotic agent, an antimicrobial agent, an immunological adjuvant, a natural product, vitamin B1, vitamin B2, vitamin B3, vitamin B5, vitamin B6, vitamin B7, vitamin B9, vitamin B12, vitamin C, or a combination thereof. In some embodiments, the interleukin inhibitor is salicylic acid. In some embodiments, the interleukin inhibitor is aspirin. In some embodiments, the interleukin inhibitor is carvacrol.

In an exemplary embodiment, the monomer-pharmaceutical conjugate is a glycerol-salicylic acid conjugate (1), which may include a mixture of mono-, di-, and tri-conjugated glycerol. The glycerol-salicylic acid conjugate (1) may be highly loaded, with many of the glycerol molecules being attached to two salicylic acid molecules, but such compositions may typically also include some molecules of glycerol attached to only one salicylic acid and some molecules of glycerol not attached to any salicylic acid:

(1)

Any of the free hydroxyl groups of the glycerol-salicylic acid conjugate (1) may covalently react with a free carboxyl group of the acid monomer. In an exemplary embodiment, the acid monomer is sebacic acid and the polyester-pharmaceutical copolymer is a PGS-salicylic acid copolymer (2) with one of a number of possible copolymer subunits being:

(2)

where R is a glycerol-salicylic acid conjugate (1).

In another embodiment, the polyester-pharmaceutical copolymer is a PGS-aspirin copolymer (3) with one of a number of possible copolymer subunits being:

(3)

In another embodiment, the monomer-pharmaceutical conjugate is a sebacic acid-carvacrol conjugate, or the polyester-pharmaceutical copolymer is a PGS-carvacrol copolymer.

In exemplary embodiments, a process to form a monomer-pharmaceutical conjugate includes a water-mediated reaction between the first monomer and the pharmaceutical compound including heating and removal of water. The pharmaceutical compound may be added with the initial charge, prior to heating under nitrogen, or prior to heating under vacuum.

In exemplary embodiments to form a monomer-pharmaceutical conjugate, the first monomer is added to a reactor vessel with water under stirring until dissolution of the first monomer. The pharmaceutical compound is provided at a molar ratio with respect to the first monomer at a ratio of 1:1 to 3:1, alternatively of 3:2 to 5:2, alternatively of 1:1 to 2:1, alternatively of 2:1 to 3:1, alternatively about 1:1, alternatively about 2:1, alternatively about 3:1, or any value, range, or sub-range therebetween. The reactor vessel is fitted with a condenser to reflux water during a reflux step, with the condenser temperature being set to 1° C. to 10° C., 1° C. to 5° C., about 5° C., about 2.5° C., or any value, range, or sub-range therebetween. The reactor vessel is then heated to a temperature of 50° C. to 200° C., alternatively 100° C. to 200° C., alternatively 125° C. to 175° C., alternatively about 140° C., alternatively about 150° C., alternatively about 160° C., or any value, range, or sub-range therebetween, under stirring for 15 to 120 minutes, alternatively 30 to 120 minutes, alternatively 45 to 90 minutes, alternatively 60 to 80 minutes, alternatively about 60 minutes, alternatively about 70 minutes, alternatively about 80 minutes, or any value, range, or sub-range therebetween.

Heat is applied to the reactor vessel of a temperature in the range of 50° C. to 200° C., alternatively 100° C. to 200° C., alternatively 125° C. to 175° C., alternatively about 140° C., alternatively about 150° C., alternatively about 160° C., or any value, range, or sub-range therebetween, and the mixture is stirred under reflux for 15 to 120 minutes, alternatively 30 to 100 minutes, alternatively 30 to 70 minutes, alternatively 40 to 60 minutes, alternatively about 40 minutes, alternatively about 50 minutes, alternatively about 60 minutes, or any value, range, or sub-range therebetween.

The condenser is then removed, and the vessel is fitted with a distillation condenser to remove water from the vessel. A nitrogen purge is applied to the vessel and heat is applied to the reactor vessel of a temperature in the range of 50° C. to 200° C., alternatively 100° C. to 200° C., alternatively 125° C. to 175° C., alternatively about 140° C., alternatively about 150° C., alternatively about 160° C., or any value, range, or sub-range therebetween. During the distillation, the contents of the vessel is stirred at 50° C. to 200° C., alternatively 100° C. to 200° C., alternatively 125° C. to 175° C., alternatively about 140° C., alternatively about 150° C., alternatively about 160° C., or any value, range, or sub-range therebetween for 1 to 48 hours, alternatively 6 to 36 hours, alternatively 12 to 36 hours, alternatively 20 to 28 hours, alternatively 22 to 26 hours, alternatively about 24 hours, or any value, range, or sub-range therebetween.

Next, a vacuum line is connected to the distillation condenser and a sub-atmospheric pressure is applied to the contents of the vessel. The pressure is reduced slowly and stepwise over 30 to 120 minutes, alternatively 50 to 120 minutes, alternatively 70 to 100 minutes, alternatively 80 to 90 minutes, alternatively about 80 minutes, alternatively about 85 minutes, alternatively about 90 minutes, or any value, range, or sub-range therebetween, to a target pressure of 30 Torr or less, alternatively 5 to 30 Torr, alternatively 20 Torr or less, alternatively 5 to 20 Torr, alternatively 10 to 20 Torr, alternatively about 15 Torr, alternatively about 20 Torr, alternatively about 25 Torr, or any value, range, or sub-range therebetween.

Once the pressure in the reaction vessel reaches the target pressure, the vacuum pump is set to a lower pressure of 20 Torr or less, alternatively 5 to 20 Torr, alternatively 10 Torr or less, alternatively 5 to 10 Torr, alternatively about 5 Torr, alternatively about 10 Torr, alternatively about 15 Torr, or any value, range, or sub-range therebetween. Following the application of vacuum, the reaction vessel is left to react at 50° C. to 200° C., alternatively 100° C. to 200° C., alternatively 125° C. to 175° C., alternatively about 140° C., alternatively about 150° C., alternatively about 160° C., or any value, range, or sub-range therebetween for 1 to 48 hours, alternatively 6 to 36 hours, alternatively 12 to 36 hours, alternatively 20 to 28 hours, alternatively 22 to 26 hours, alternatively about 24 hours, or any value, range, or sub-range therebetween, under stirring, with the sub-atmospheric pressure set to the lower pressure.

In exemplary embodiments, a process to form a polyester-pharmaceutical copolymer from a monomer-pharmaceutical conjugate includes a water-mediated reaction between the monomer-pharmaceutical conjugate and a second monomer including heating and removal of water.

In exemplary embodiments to form a polyester-pharmaceutical copolymer, a first monomer and a monomer-pharmaceutical conjugate are added to a reactor vessel with water under stirring. After dissolution of the first monomer and the monomer-pharmaceutical conjugate, a second monomer is added to the reactor vessel. The amounts of the first monomer, the monomer-pharmaceutical conjugate, and the second monomer are selected to provide a predetermined molar ratio of free hydroxyl groups to free carboxyl groups of 1:2 to 2:1, alternatively 1:1 to 2:1, alternatively 5:4 to 7:4, alternatively about 5:4, alternatively about 3:2, alternatively about 7:4, or any ratio, range, or sub-range therebetween. The reactor vessel is then fitted with a condenser to reflux water during the melt and stir steps of the polymerization, with the condenser temperature being set to 1° C. to 10° C., 1° C. to 5° C., about 5° C., about 2.5° C., or any range, or sub-range therebetween. Heat is applied to the reactor vessel of a temperature in the range of 50° C. to 200° C., alternatively 100° C. to 180° C., alternatively 115° C. to 165° C., alternatively about 130° C., alternatively about 140° C., alternatively about 150° C., or any value, range, or sub-range therebetween, under stirring for 15 to 120 minutes, alternatively 30 to 120 minutes, alternatively 45 to 90 minutes, alternatively 60 to 80 minutes, alternatively about 60 minutes, alternatively about 70 minutes, alternatively about 80 minutes, or any value, range, or sub-range therebetween.

After the second monomer melts, heat is applied to the reactor vessel of a temperature in the range of 50° C. to 200° C., alternatively 100° C. to 160° C., alternatively 120° C. to 140° C., alternatively about 120° C., alternatively about 130° C., alternatively about 140° C., or any value, range, or sub-range therebetween, and the mixture is stirred under reflux for 15 to 120 minutes, alternatively 30 to 90 minutes, alternatively 40 to 60 minutes, alternatively about 40 minutes, alternatively about 50 minutes, alternatively about 60 minutes, or any value, range, or sub-range therebetween.

The condenser is then removed, and the vessel is fitted with a distillation condenser to remove water from the vessel. A nitrogen purge is applied to the vessel and heat is applied to the reactor vessel of a temperature in the range of 50° C. to 200° C., alternatively 100° C. to 140° C., alternatively 110° C. to 130° C., alternatively about 110° C., alternatively about 120° C., alternatively about 130° C., or any value, range, or sub-range therebetween. During the distillation, the contents of the vessel are stirred at 50° C. to 200° C., alternatively 100° C. to 140° C., alternatively 110° C. to 130° C., alternatively about 110° C., alternatively about 120° C., alternatively about 130° C., or any value, range, or sub-range therebetween, for 1 to 48 hours, alternatively 6 to 36 hours, alternatively 12 to 36 hours, alternatively 20 to 28 hours, alternatively 22 to 26 hours, alternatively about 24 hours, or any value, range, or sub-range therebetween.

Next, a vacuum line is connected to the distillation condenser and the sub-atmospheric pressure is applied to the contents of the vessel. The pressure is reduced slowly and stepwise over 15 to 120 minutes, alternatively 30 to 120 minutes, alternatively 60 to 110 minutes, alternatively 75 to 95 minutes, alternatively about 75 minutes, alternatively about 85 minutes, alternatively about 95 minutes, or any value, range, or sub-range therebetween, to a target pressure of 30 Torr or less, alternatively 5 to 30 Torr, alternatively 20 Torr or less, alternatively 5 to 20 Torr, alternatively 10 to 20 Torr, alternatively about 15 Torr, alternatively about 20 Torr, alternatively about 25 Torr, or any value, range, or sub-range therebetween.

Once the pressure in the reaction vessel reaches the target pressure, the vacuum pump is set to a lower pressure of 20 Torr or less, alternatively 5 to 20 Torr, alternatively 10 Torr or less, alternatively 5 to 10 Torr, alternatively about 5 Torr, alternatively about 10 Torr, alternatively about 15 Torr, or any value, range, or sub-range therebetween. Following the application of vacuum, the reaction vessel is left to react for 1 to 48 hours, alternatively 6 to 36 hours, alternatively 12 to 36 hours, alternatively 22 to 30 hours, alternatively 24 to 28 hours, alternatively about 26 hours, or any value, range, or sub-range therebetween, at 50° C. to 200° C., alternatively 100° C. to 160° C., alternatively 120° C. to 140° C., alternatively about 120° C., alternatively about 130° C., alternatively about 140° C., or any value, range, or sub-range therebetween, under stirring, with the sub-atmospheric pressure set to the lower pressure.

Next, the product in the reactor vessel is transferred to a glass jar and allowed to cool on the bench top for about 15 to 120 minutes, alternatively 30 to 90 minutes, alternatively 35 to 55 minutes, alternatively about 35 minutes, alternatively about 45 minutes, alternatively about 55 minutes, or any value, range, or sub-range therebetween, then is transferred to a freezer for storage, where it is frozen for at least 12 hours, alternatively at least 18 hours, alternatively at least about 24 hours, or alternatively at least 48 hours before testing and analysis.

In alternative embodiments not involving using a monomer-pharmaceutical conjugate, a process to form a polyester-pharmaceutical copolymer from a polyester copolymer and a pharmaceutical compound includes a water-mediated reaction between the polyester and the pharmaceutical compound including heating and removal of water.

In such alternative embodiments, the polyester copolymer is added to a reactor vessel with water under stirring. The pharmaceutical compound is then added to the reactor vessel. The pharmaceutical compound is provided at 0.1% to 10%, alternatively 0.1% to 5%, alternatively 5% to 10%, alternatively 1% to 5%, alternatively 0.1% to 2%, alternatively about 1%, by weight, based on the combined weight of the pharmaceutical compound and the polyester copolymer. The reactor vessel is then fitted with a distillation condenser to remove water from the vessel. Heat is applied to the reactor vessel of a temperature in the range of 50° C. to 200° C., alternatively 100° C. to 160° C., alternatively 120° C. to 140° C., alternatively about 120° C., alternatively about 130° C., alternatively about 140° C., or any value, range, or sub-range therebetween, under stirring for 15 to 120 minutes, alternatively 30 to 120 minutes, alternatively 45 to 90 minutes, alternatively 60 to 80 minutes, alternatively about 60 minutes, alternatively about 70 minutes, alternatively about 80 minutes, or any value, range, or sub-range therebetween.

Next, a vacuum line is connected to the distillation condenser and a sub-atmospheric pressure is applied to the contents of the vessel. The pressure is reduced slowly and stepwise over about 15 to 120 minutes, alternatively 30 to 120 minutes, alternatively 60 to 110 minutes, alternatively 75 to 95 minutes, alternatively about 75 minutes, alternatively about 85 minutes, alternatively about 95 minutes, or any value, range, or sub-range therebetween, to a target pressure of 30 Torr or less, alternatively 5 to 30 Torr, alternatively 20 Torr or less, alternatively 5 to 20 Torr, alternatively 10 to 20 Torr, alternatively about 15 Torr, alternatively about 20 Torr, alternatively about 25 Torr, or any value, range, or sub-range therebetween.

Once the pressure in the reaction vessel reaches the target pressure, the vacuum pump is set to a lower pressure of 20 Torr or less, alternatively 5 to 20 Torr, alternatively 10 Torr or less, alternatively 5 to 10 Torr, alternatively about 5 Torr, alternatively about 10 Torr, alternatively about 15 Torr, or any value, range, or sub-range therebetween. Following the application of vacuum, the reaction vessel is left to react for 1 to 48 hours, alternatively 6 to 36 hours, alternatively 12 to 36 hours, alternatively 20 to 28 hours, alternatively 22 to 26 hours, alternatively about 24 hours, or any value, range, or sub-range therebetween, at 50° C. to 200° C., alternatively 100° C. to 160° C., alternatively 120° C. to 140° C., alternatively about 120° C., alternatively about 130° C., alternatively about 140° C., or any value, range, or sub-range therebetween, under stirring, with the sub-atmospheric pressure set to the lower pressure.

A polyester-pharmaceutical copolymer may be used in a variety of applications, including, but not limited to, periodontal treatments, bone growth control, wound care, medical device coatings, cardiac stents, cardiovascular grafts, cardiovascular patches, treating cardiovascular disorders, adhesion barriers, surgical meshes, in dermatology indications, in personal care products, in cosmetic products, biofilm prevention, biofilm mitigation, steroid-sparing joint pain injectables, opiate controlled release, nerve guides, nerve conduits, urinary catheters, biodegradable polymer microspheres, dose delivery, cancer therapy, cell therapy, bioreactor technology, chemotherapy tumor site implantation, oral antimicrobials, or polymer stabilization.

A polyester-pharmaceutical copolymer may form at least part of a variety of articles or devices, including, but not limited to, microspheres, microparticles, embolic delivery devices, targeted delivery devices, device coatings, implants, or implant coatings, such as the articles or devices disclosed in U.S. patent application Ser. No. 15/941,745, which is hereby incorporated by reference in its entirety.

EXAMPLES

The invention is further described in the context of the following examples which are presented by way of illustration, not of limitation.

Example 1

A PGS-salicylic acid copolymer was formed in a water-mediated reaction from glycerol, sebacic acid, and salicylic acid, where the initial charge of the reactor vessel included the glycerol, salicylic acid, sebacic acid, and water.

The glycerol, salicylic acid, sebacic acid, and water were added under stirring. Equimolar amounts of glycerol and sebacic acid were used, and the salicylic acid was provided at 1% by weight based on the combined weight of the glycerol, sebacic acid, and salicylic acid reagents. The reactor vessel was then fitted with a condenser to reflux water during the melt and stir steps of the polymerization, with the condenser temperature being set to 2.5° C. (36.5° F.). Heat is applied to the reactor vessel of a temperature of 140° C. (284° F.) under stirring for approximately 70 minutes.

After the sebacic acid melted, heat was applied to the reactor vessel of a temperature of 130° C. (266° F.) and the mixture was stirred under reflux for 50 minutes.

The condenser was then removed, and the vessel was fitted with a distillation condenser to remove water from the vessel. A nitrogen purge was applied to the vessel and heat is applied to the reactor vessel of a temperature of 120° C. During the distillation, the contents of the vessel were stirred at 120° C. for 24 hours.

Next, a vacuum line was connected to the distillation condenser and the sub-atmospheric pressure was applied to the contents of the vessel. The pressure was reduced slowly and stepwise over about 85 minutes to approximately 20 Torr.

Once the pressure in the reaction vessel reached approximately 20 Torr, the vacuum pump was set to 10 Torr. Following the application of vacuum, the reaction vessel was left to react for 26 hours at 130° C. under stirring, with the sub-atmospheric pressure set to 10 Torr.

Next, the PGS material in the reactor vessel was transferred to a glass jar and allowed to cool on the bench top for about 45 minutes, then was transferred to a freezer for storage, where it was frozen for at least about 24 hours before testing and analysis.

Salicylic acid, which melts at about 158° C. (316° F.) and sublimes at about 76° C. (169° F.), was found crystallized on the lid, the condenser, and the Schlenk line after the synthesis.

Ultraviolet/visible light (UV/Vis) analysis at a wavelength of 303 nanometers (nm) to detect the salicylic acid indicated the presence of a total amount of 0.6% salicylic acid, by weight.

Gel permeation chromatography (GPC) analysis at a wavelength of 303 nm to detect the salicylic acid indicated a conjugated amount of 0.32% salicylic acid, by weight.

Figure 1:
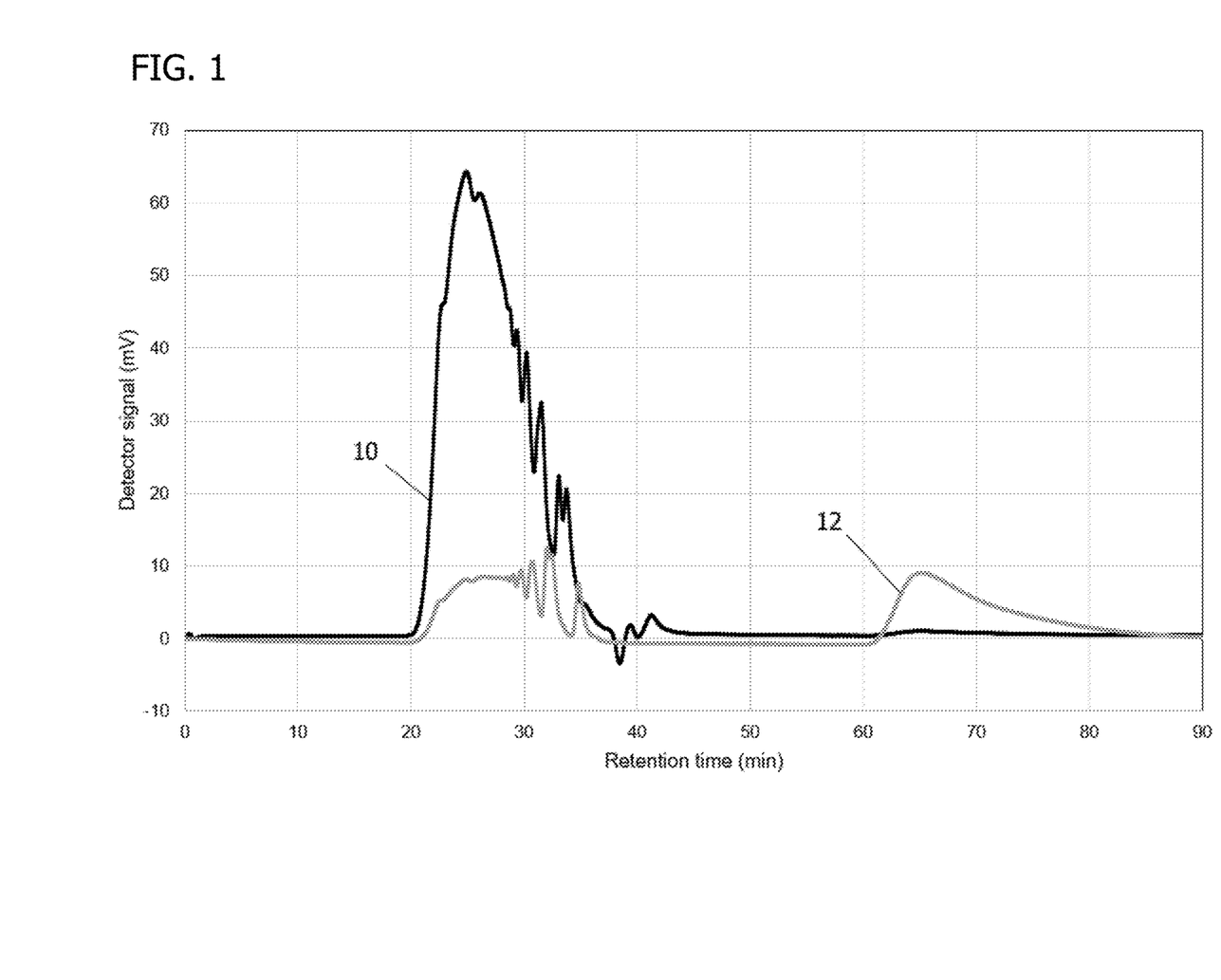
FIG. 1 shows gel permeation chromatography (GPC) chromatograms for a PGS-salicylic acid copolymer formed from a single reaction charge.

FIG. 1 shows the GPC chromatograms for the resulting PGS-salicylic acid copolymer. The black line represents the refractive index (RI) chromatogram 10 and the gray line represents the UV/Vis chromatogram 12 at 303 nm. The UV/Vis chromatogram detects the presence of the salicylic acid. The peaks at less than 40 minutes indicate that salicylic acid was incorporated into the copolymer across the molecular weights of the PGS-salicylic acid copolymer. The peak at greater than 60 minutes indicates that not all of the salicylic acid was incorporated into the copolymer.

Example 2

A PGS-salicylic acid copolymer was formed in a water-mediated reaction from glycerol, sebacic acid, and salicylic acid, where the salicylic acid was added after the distillation step.

The procedure of Example 1 was repeated, except that the salicylic acid was not added with the initial charge but instead was added between the distillation step and the vacuum step.

Salicylic acid was again found crystallized on the lid, the condenser, and the Schlenk line after synthesis.

UV/Vis analysis at a wavelength of 303 nanometers (nm) to detect the salicylic acid indicated the presence of a total amount of 0.55% salicylic acid, by weight.

Figure 2:
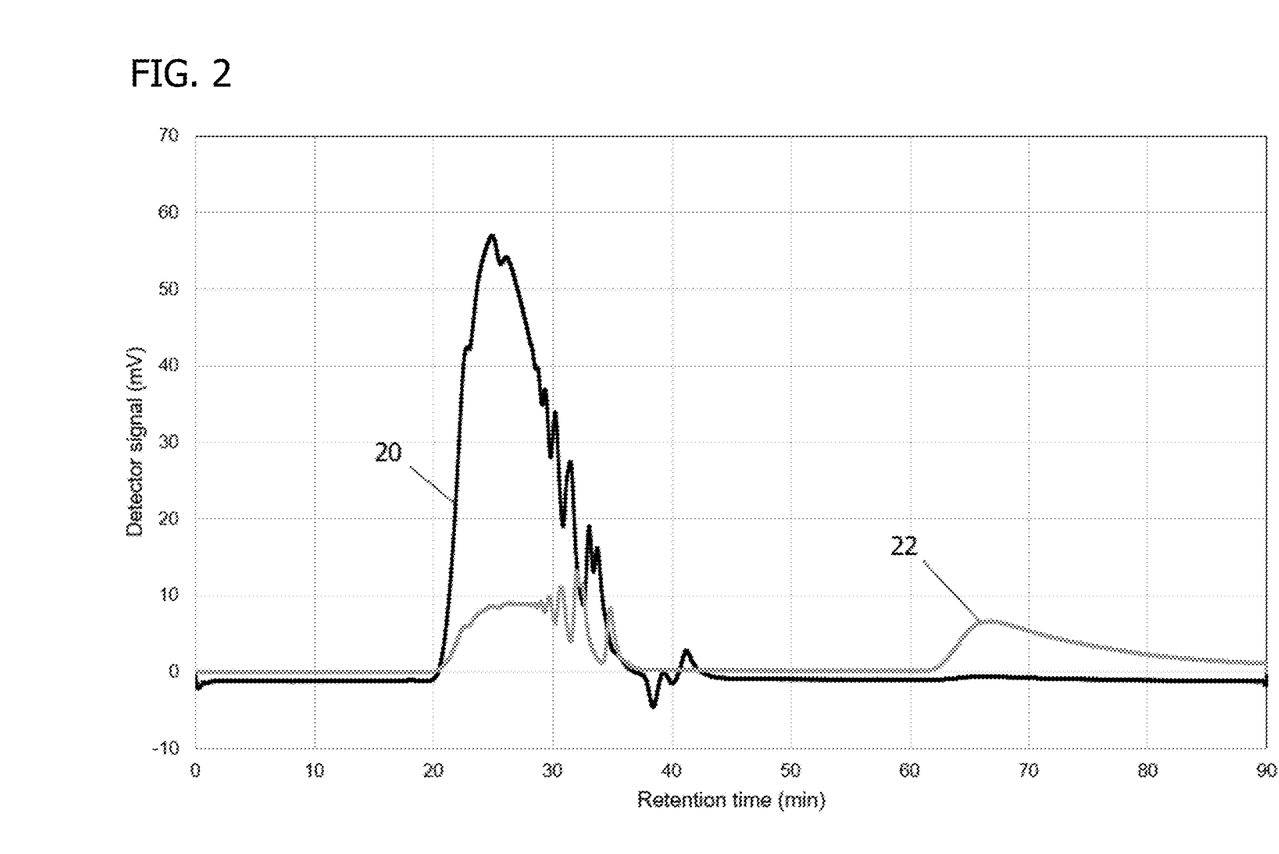
FIG. 2 shows GPC chromatograms for a PGS-salicylic acid copolymer formed in a single reactor with the salicylic acid being added after the distillation step.

GPC analysis at a wavelength of 303 nm to detect the salicylic acid indicated a conjugated amount of 0.29% salicylic acid, by weight. FIG. 2 shows the GPC chromatograms for the resulting PGS-salicylic acid copolymer. As in FIG. 1, the black line represents the RI chromatogram 20 and the gray line represents the UV/Vis chromatogram 22 at 303 nm. Again, the peaks at less than 40 minutes indicate that salicylic acid was incorporated into the copolymer across the molecular weights of the PGS-salicylic acid copolymer, and the peak at greater than 60 minutes indicates that not all of the salicylic acid was incorporated into the copolymer, with more of the salicylic acid being incorporated into the copolymer than in Example 1.

Example 3

A glycerol-salicylic acid conjugate was formed in a water-mediated reaction from glycerol and salicylic acid, where the initial charge of the reactor vessel included the glycerol, salicylic acid, and water.

The glycerol, salicylic acid, and water were added under stirring. The salicylic acid was provided at a 2:1 molar ratio with respect to the amount of glycerol. The reactor vessel was then fitted with a condenser to reflux water during a reflux step, with the condenser temperature being set to 2.5° C. Heat was applied to the reactor vessel of a temperature of 150° C. (302° F.) under stirring for approximately 70 minutes.

Heat was applied to the reactor vessel of a temperature of 150° C. and the mixture was stirred under reflux for 50 minutes.

The condenser was then removed, and the vessel was fitted with a distillation condenser to remove water from the vessel. A nitrogen purge was applied to the vessel and heat was applied to the reactor vessel of a temperature of 150° C. During the distillation, the contents of the vessel were stirred at 150° C. for 24 hours.

Samples were removed after this distillation step and characterized.

The resulting glycerol-salicylic acid conjugate was viscous with a brown color and a sweet smell.

Figure 3:
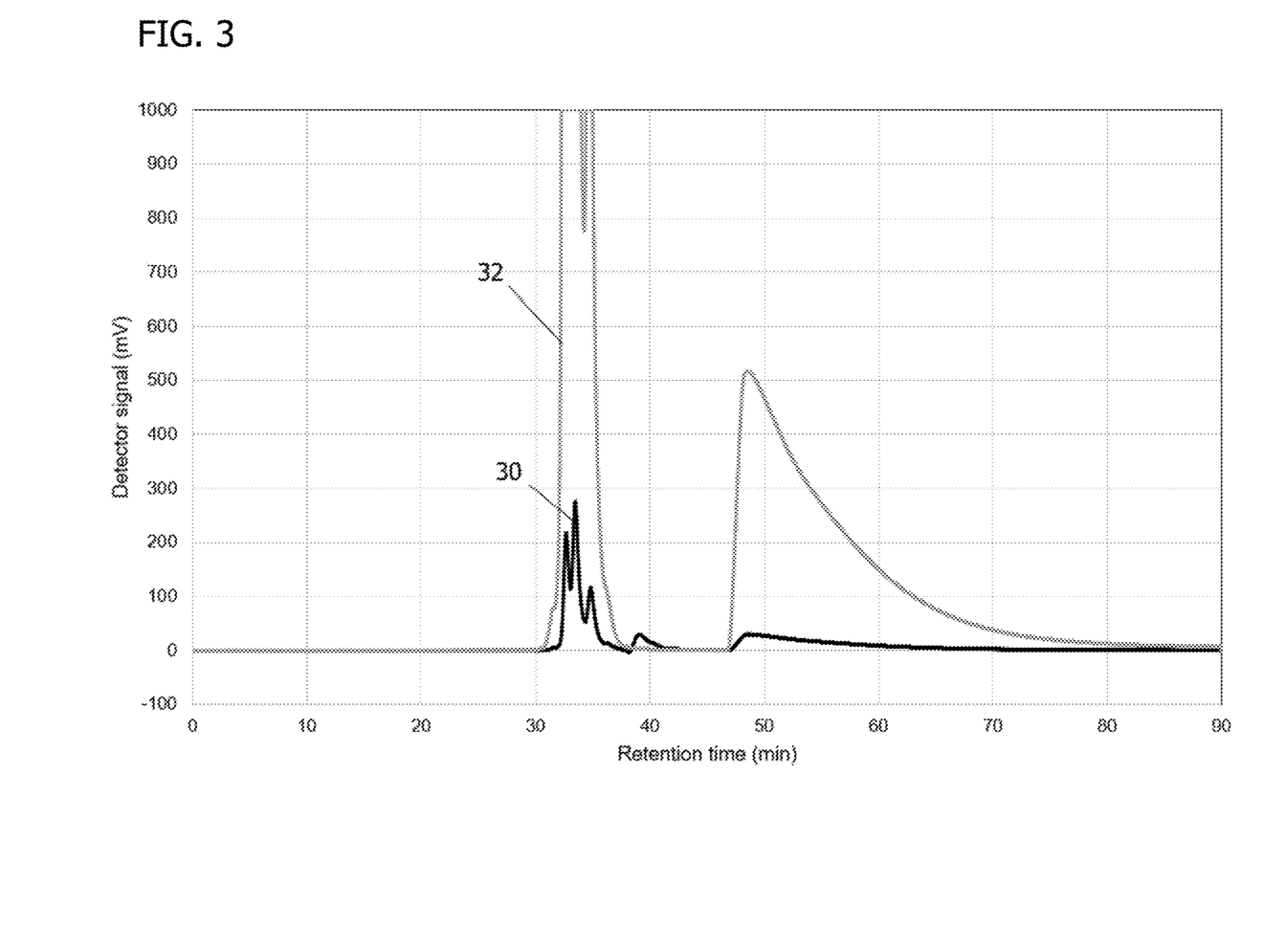
FIG. 3 shows GPC chromatograms for a glycerol-salicylic acid conjugate formed from a single reaction charge after an initial distillation.

The structure was characterized by UV/Vis at a wavelength of 303 nm. GPC analysis at a wavelength of 303 nm to detect the salicylic acid indicated a conjugated amount of at least 40% salicylic acid, by weight. No polymerization was detected in the GPC analysis. FIG. 3 shows the GPC chromatograms for the resulting glycerol-salicylic acid conjugate. Again, the black line represents the RI chromatogram 30 and the gray line represents the UV/Vis chromatogram 32 at 303 nm. The peaks at less than 40 minutes indicate formation of glycerol-salicylic acid conjugate, but the peak at greater than 60 minutes indicates that not all of the salicylic acid was conjugated.

Example 4

Next, a vacuum line was connected to the distillation condenser and the sub-atmospheric pressure was applied to the remaining contents of the reaction vessel from Example 3. The pressure was reduced slowly and stepwise over about 85 minutes to approximately 20 Torr.

Once the pressure in the reaction vessel reached approximately 20 Torr, the vacuum pump was set to 10 Torr. Following the application of vacuum, the reaction vessel was left to react for 24 hours at 150° C. under stirring, with the sub-atmospheric pressure set to 10 Torr.

The resulting glycerol-salicylic acid conjugate was viscous with a brown color and a sweet smell.

Figure 4:
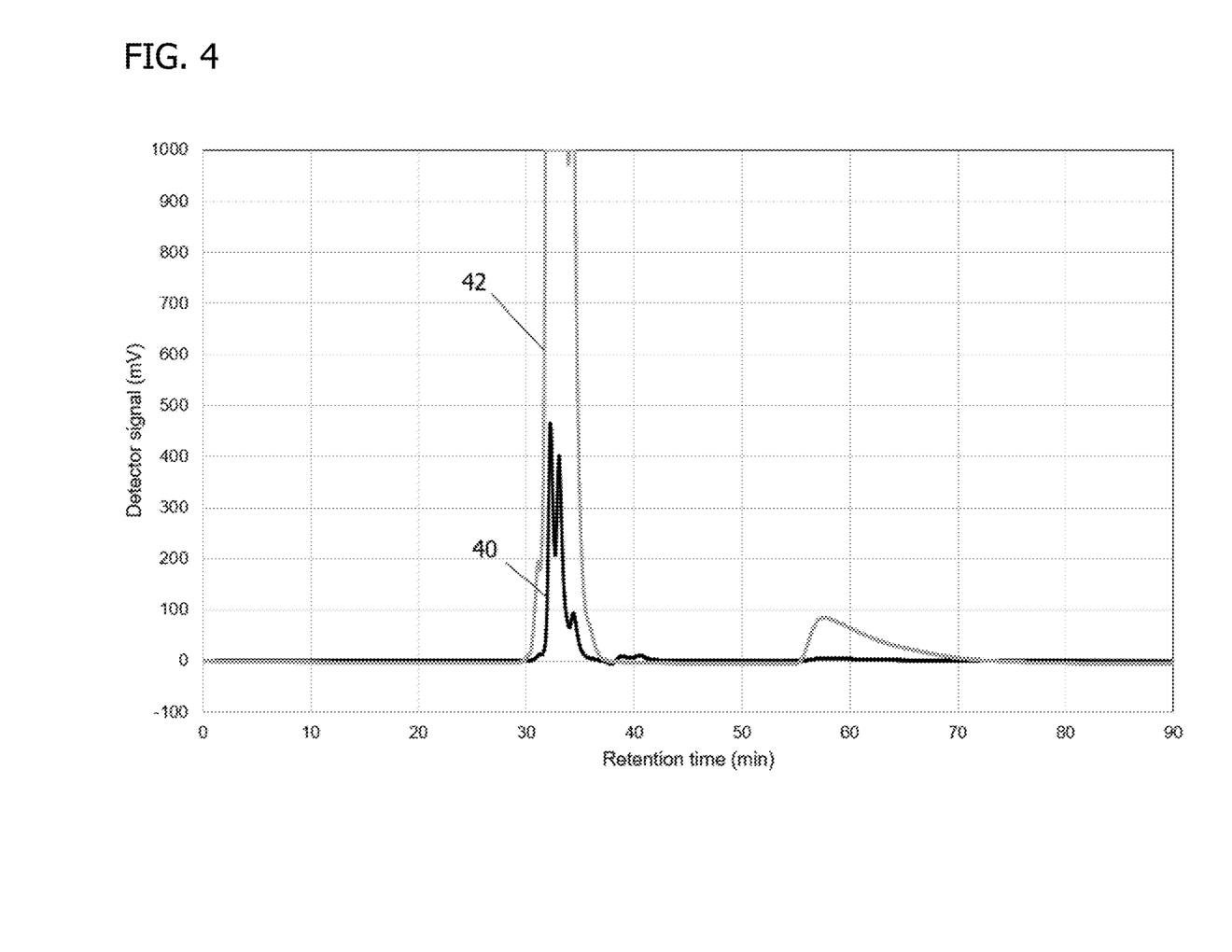
FIG. 4 shows GPC chromatograms for a glycerol-salicylic acid conjugate formed from a single reaction charge after additional vacuum heating.

The structure was characterized by UV/Vis at a wavelength of 303 nm. GPC analysis at a wavelength of 303 nm to detect the salicylic acid indicated a conjugated amount of at least 83% salicylic acid, by weight. No polymerization was detected in the GPC analysis. FIG. 4 shows the GPC chromatograms for the resulting glycerol-salicylic acid conjugate. Again, the black line represents the RI chromatogram 40 and the gray line represents the UV/Vis chromatogram 42 at 303 nm. The shift in the relative peak sizes in the UV/Vis chromatogram indicates a higher level of salicylic acid conjugation than in Example 3.

Example 5

A PGS-salicylic acid copolymer was formed in a water-mediated reaction from glycerol, glycerol-salicylic acid conjugate, and sebacic acid.

Glycerol and a glycerol-salicylic acid conjugate from Example 4 were added to a reactor vessel with water under stirring. After dissolution of the glycerol and glycerol-salicylic acid conjugate, sebacic acid was added to the reactor vessel. The amounts of glycerol, glycerol-salicylic acid conjugate, and sebacic acid were selected to provide a 3:2 molar ratio of free hydroxyl groups to free carboxyl groups, assuming the glycerol-salicylic acid conjugate to be 80% by weight salicylic acid. The reactor vessel was then fitted with a condenser to reflux water during the melt and stir steps of the polymerization, with the condenser temperature being set to 2.5° C. Heat was applied to the reactor vessel of a temperature of 140° C. under stirring for approximately 70 minutes.

After the sebacic acid melted, heat was applied to the reactor vessel of a temperature of 130° C. and the mixture was stirred under reflux for 50 minutes.

The condenser was then removed, and the vessel was fitted with a distillation condenser to remove water from the vessel. A nitrogen purge was applied to the vessel and heat was applied to the reactor vessel of a temperature of 120° C. During the distillation, the contents of the vessel were stirred at 120° C. for 24 hours.

Next, a vacuum line was connected to the distillation condenser and the sub-atmospheric pressure was applied to the contents of the vessel. The pressure was reduced slowly and stepwise over about 85 minutes to approximately 20 Torr.

Once the pressure in the reaction vessel reached approximately 20 Torr, the vacuum pump was set to 10 Torr. Following the application of vacuum, the reaction vessel was left to react for 26 hours at 130° C. under stirring, with the sub-atmospheric pressure set to 10 Torr.

After this period, the PGS material in the reactor vessel was transferred to a glass jar and allowed to cool on the bench top for about 45 minutes, then was transferred to a freezer for storage, where it was frozen for at least about 24 hours before testing and analysis.

Figure 5:
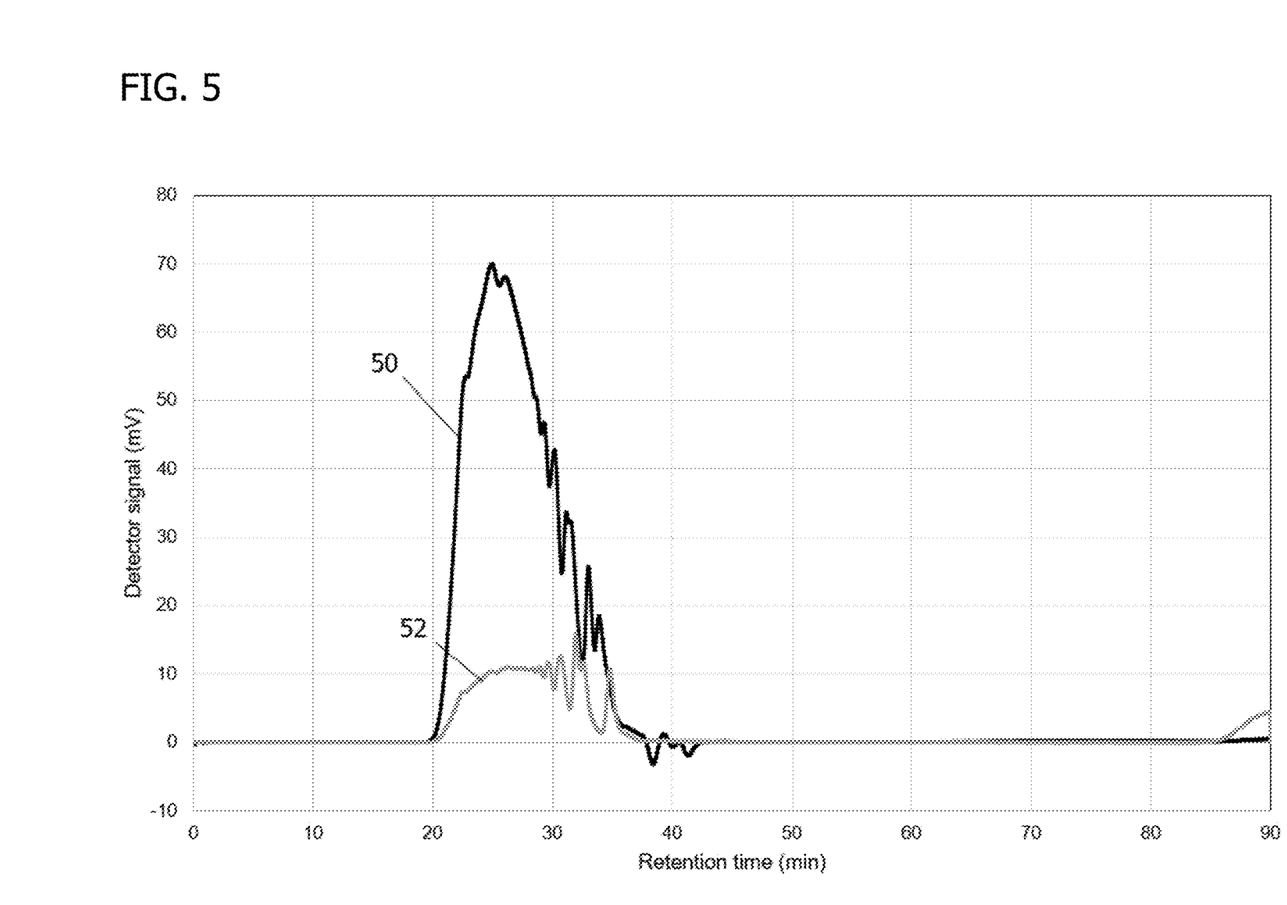
FIG. 5 shows GPC chromatograms for a PGS-salicylic acid copolymer formed from a PGS-salicylic acid copolymer and sebacic acid.

The structure was characterized by 1H-NMR and GPC. UV/Vis analysis at a wavelength of 303 nanometers (nm) to detect the salicylic acid indicated the presence of a total amount of 24.6% and 25.1% salicylic acid, by weight, in two separate runs, indicating about 97% and 99% theoretical incorporation of the salicylic acid. FIG. 5 shows the GPC chromatograms for the resulting PGS-salicylic acid copolymer. Again, the black line represents the RI chromatogram 50 and the gray line represents the UV/Vis chromatogram 52 at 303 nm. Again, the peaks at less than 40 minutes indicate that salicylic acid was incorporated into the copolymer across the molecular weights of the PGS-salicylic acid copolymer, and the lack of a peak at greater than 60 minutes indicates that nearly all of the salicylic acid was incorporated into the copolymer.

Example 6

A PGS-aspirin copolymer was formed in a water-mediated reaction from PGS and aspirin.

PGS, formed by a water-mediated process as disclosed in U.S. Pat. No. 9,359,472, was added to a reactor vessel with water under stirring. Aspirin was then added to the reactor vessel. The aspirin was provided at 1% by weight based on the combined weight of the aspirin and PGS. The reactor vessel was then fitted with a distillation condenser to remove water from the vessel. Heat was applied to the reactor vessel of a temperature of 130° C. under stirring for approximately 70 minutes.

Next, a vacuum line was connected to the distillation condenser and the sub-atmospheric pressure was applied to the contents of the vessel. The pressure was reduced slowly and stepwise over about 85 minutes to approximately 20 Torr.

Once the pressure in the reaction vessel reached approximately 20 Torr, the vacuum pump was set to 10 Torr. Following the application of vacuum, the reaction vessel was left to react for 24 hours at 130° C. under stirring, with the sub-atmospheric pressure set to 10 Torr.

Figure 6:
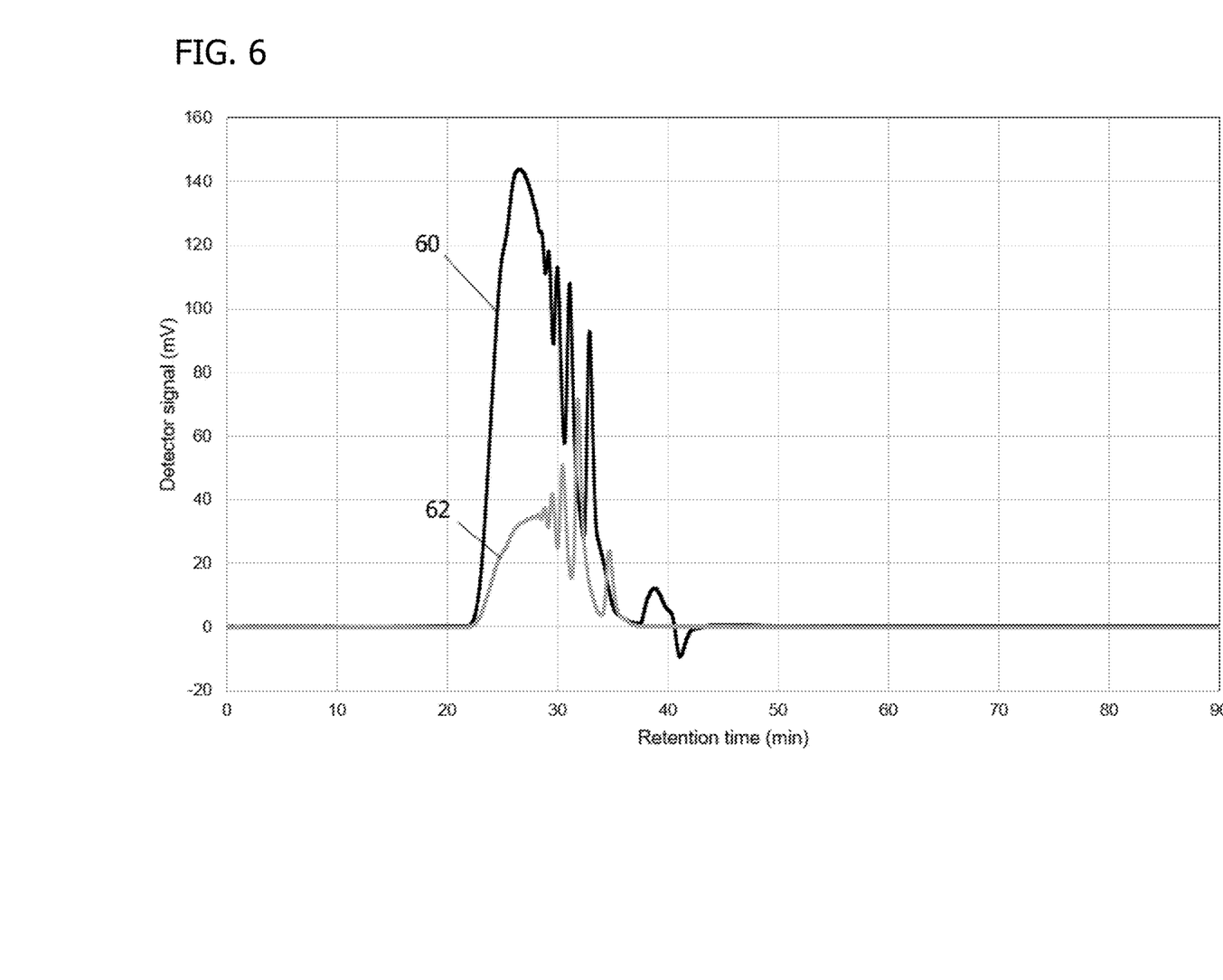
FIG. 6 shows GPC chromatograms for a PGS-aspirin copolymer formed from a single reaction charge.

UV/Vis analysis at a wavelength of 303 nanometers (nm) to detect the aspirin indicated the presence of a total amount of 0.89% aspirin, by weight. FIG. 6 shows the GPC chromatograms for the resulting PGS-aspirin copolymer. Again, the black line represents the RI chromatogram 60 and the gray line represents the UV/Vis chromatogram 62 at 303 nm. The peaks at less than 40 minutes indicate that aspirin was incorporated into the copolymer across the molecular weights of the PGS-aspirin copolymer, and the lack of a peak at greater than 60 minutes indicates that nearly all of the aspirin was incorporated into the copolymer.

The PGS-aspirin copolymer had a weight average molecular weight (Mw) of about 5,600 Da and thermoset well only at temperatures greater than 130° C.

Example 7

A PGS-salicylic acid copolymer from Example 5 was thermoset by heating to 130° C. at a pressure of 10 Torr for 48 hours. Three thin cylindrical disks, each having a diameter of 10 mm, were punched out of the resultant thin film, which was about 1 mm thick.

Each disk was placed in 10 mL of 0.09 M phosphate-buffered saline (PBS) at a pH of 11 and a temperature of 37° C. for four weeks. At 1-week intervals, the solution was removed and tested for salicylic acid content by UV analysis at a wavelength of 303 nm and for pH. Each sample was rinsed three times with distilled water and vacuum dried prior to being placed in fresh PBS.

Figure 7:
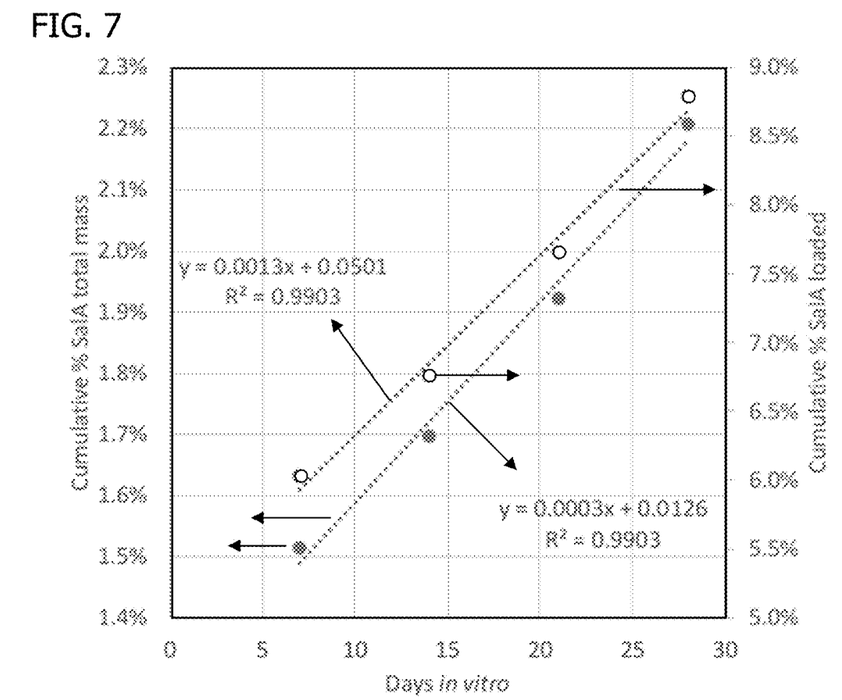
FIG. 7 shows salicylic acid release by degradation of a thermoset PGS-salicylic acid copolymer.

FIG. 7 shows the calculated average cumulative percentage of salicylic acid loss based on the starting total mass of the disk and based on the starting total loading of salicylic acid for the three samples. After an initial bolus release, the salicylic acid release was linear between days 7 and 28, with about 8.8% of the salicylic acid having been released by 28 days. The linear release after day 7 indicates degradation of the thermoset disk based on surface erosion.

Figure 8:
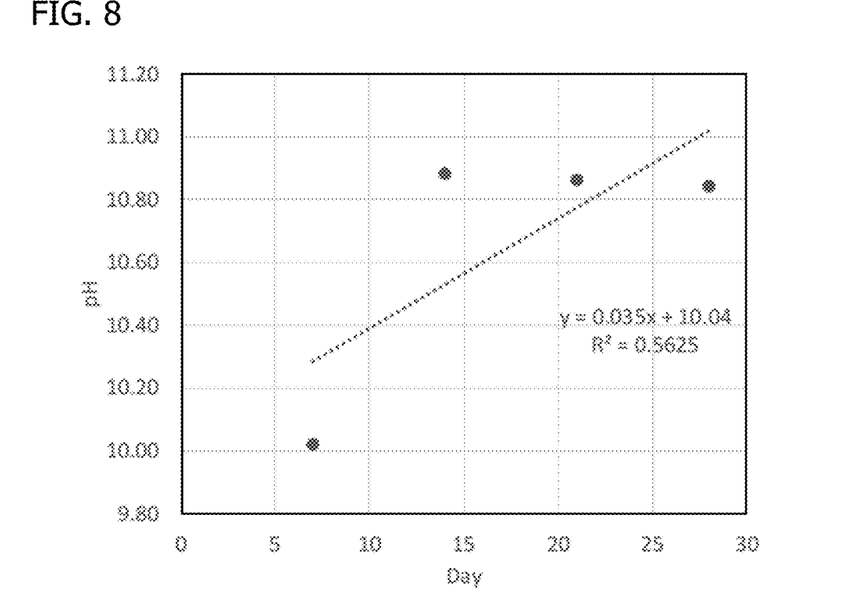
FIG. 8 shows the pH of the buffer at each data point during the degradation study of FIG. 7.

FIG. 8 shows the average pH of the buffer for the three samples after each 7-day time period. The bolus release dropped the pH of the buffer to about 10 after 7 days. During the linear release, however, the pH of the buffer was fairly stable and was measured as being between 10.8 and 10.9.

Example 8

A PGS-aspirin copolymer from Example 6 was thermoset by heating to 130° C. at a pressure of 10 Torr for 72 hours.

Three thin cylindrical disks, each having a diameter of 10 mm, were punched out of the resultant thin film, which was about 1 mm thick.

Each disk was placed in 10 mL of 0.09 M phosphate-buffered saline (PBS) at a pH of 11 and a temperature of 37° C. for four weeks. At 1-week intervals, the solution was removed and tested for salicylic acid content by UV analysis at a wavelength of 303 nm and for pH. Each sample was rinsed three times with distilled water and vacuum dried prior to being placed in fresh PBS.

Figure 9:
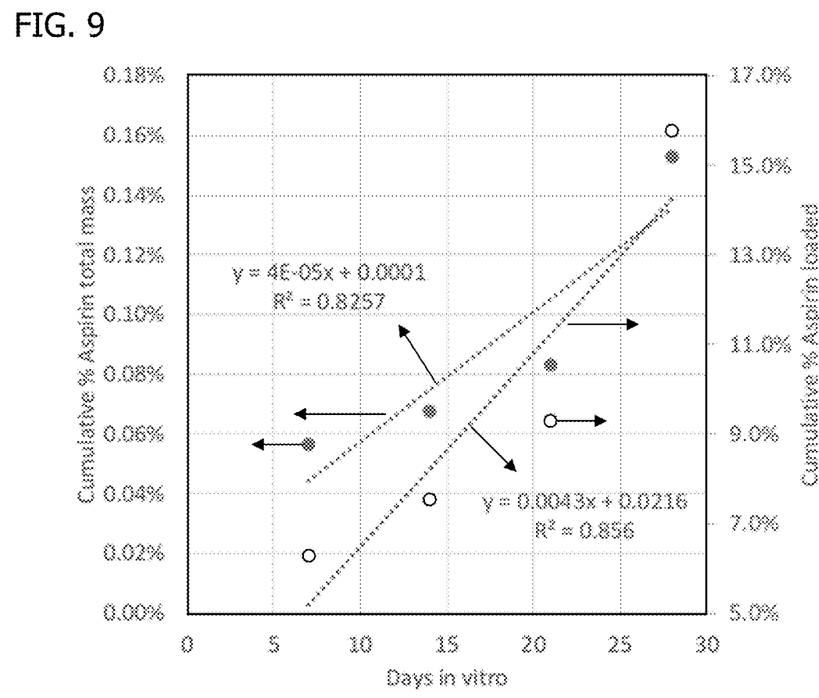
FIG. 9 shows aspirin release by degradation of a thermoset PGS-salicylic acid copolymer.

FIG. 9 shows the calculated average cumulative percentage of aspirin loss based on the starting total mass of the disk and based on the starting total loading of aspirin for the three samples. After an initial bolus release, the aspirin release was nearly linear between days 7 and 21, with about 9.2% of the aspirin having been released by 21 days. Between day 21 and day 28, however, the disks began to fall apart, leading to the increased amount of loss observed during that fourth week. The burst-linear-burst release indicates a significantly less crosslinked copolymer.

Figure 10:
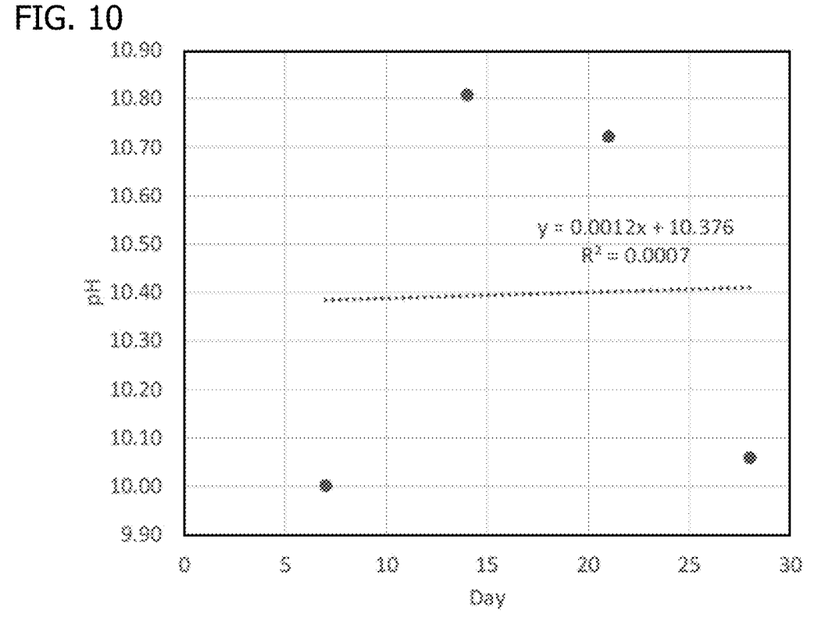
FIG. 10 shows the pH of the buffer at each data point during the degradation study of FIG. 9.

FIG. 10 shows the average pH of the buffer for the three samples after each 7-day time point. The bolus release dropped the pH of the buffer to about 10 after 7 days. During the linear release, however, the pH of the buffer was fairly stable and was measured as being between 10.7 and 10.8. During the fourth week, however, the rapid release dropped the pH to between 10.0 and 10.1.

All above-mentioned references are hereby incorporated by reference herein.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of preparing a polymeric material, comprising the steps of:
   combining glycerol, a glycerol-pharmaceutical conjugate, and water in a vessel, the glycerol-pharmaceutical conjugate comprising a pharmaceutical compound having at least one carboxyl group attached to the glycerol by an ester bond; then
   adding sebacic acid to the vessel; then
   removing water from the vessel and reacting the glycerol, glycerol-pharmaceutical conjugate, and sebacic acid in the vessel at atmospheric pressure and a temperature in the range of 50-200° C. in the presence of an inert gas for a period of about 1 hour to about 48 hours; and then
   applying a sub-atmospheric pressure to the vessel for about 1 hour to about 76 hours after the step of reacting in the presence of an inert gas at atmospheric pressure, with a temperature in the vessel in the range of 50-200° C., thereby forming the polymeric material in the vessel, the polymeric material comprising a polyester copolymer of the sebacic acid and the glycerol and the pharmaceutical compound;
   wherein the pharmaceutical compound is salicylic acid.

2. The method of claim 1, wherein the sub-atmospheric pressure is in the range of 5 Torr to 20 Torr.

3. The method of claim 1, wherein the sub-atmospheric pressure is applied for about 24 hours to about 36 hours.

4. The method of claim 1, wherein the polymeric material includes 20% to 25% of the salicylic acid, by weight, based on the total weight of the polymeric material.

5. The method of claim 1, wherein the removing water from the vessel comprises refluxing the glycerol-pharmaceutical conjugate, the glycerol, the water, and the sebacic acid.

6. The method of claim 1 further comprising adding an additional co-monomer to the vessel to form the polymeric material incorporating the additional co-monomer.

7. The method of claim 6, wherein the additional co-monomer is selected from the group consisting of lactic acid and caprolactone.

* * * * *